(12) United States Patent
Frisch et al.

(10) Patent No.: US 8,110,529 B2
(45) Date of Patent: Feb. 7, 2012

(54) CONCENTRATED, WATER-BASED DISPERSIONS FOR CROP PROTECTION

(75) Inventors: Gerhard Frisch, Wehrheim (DE); Thomas Maier, Hofheim (DE)

(73) Assignee: Bayer Cropscience AG, Monheim (DE)

( * ) Notice: Subject to any disclaimer, the term of this patent is extended or adjusted under 35 U.S.C. 154(b) by 663 days.

(21) Appl. No.: 11/140,001

(22) Filed: May 27, 2005

(65) Prior Publication Data
US 2005/0266995 A1  Dec. 1, 2005

(30) Foreign Application Priority Data
Jun. 1, 2004  (DE) .......... 10 2004 026 935

(51) Int. Cl.
*A01N 63/00*  (2006.01)
(52) U.S. Cl. ......... 504/118; 504/127; 504/130; 504/132
(58) Field of Classification Search ............... 504/116.1, 504/118, 127, 130, 132
See application file for complete search history.

(56) References Cited

U.S. PATENT DOCUMENTS

| | | | |
|---|---|---|---|
| 3,799,758 A | 3/1974 | Franz et al. | |
| 4,351,754 A | 9/1982 | Dupre et al. | |
| 4,400,196 A | 8/1983 | Albrecht et al. | |
| 4,868,321 A * | 9/1989 | Theodoridis | 558/17 |
| 5,125,823 A | 6/1992 | Kreyenborg | |
| 5,147,444 A * | 9/1992 | Decor et al. | 504/127 |
| 5,341,932 A * | 8/1994 | Chen et al. | 206/524.7 |
| 5,563,112 A * | 10/1996 | Barnes, III | 504/125 |
| 5,595,958 A * | 1/1997 | Chin et al. | 504/250 |
| 5,670,453 A * | 9/1997 | Chin et al. | 504/235 |
| 5,707,930 A * | 1/1998 | Felix et al. | 504/197 |
| 5,795,847 A * | 8/1998 | Nielsen et al. | 504/206 |
| 5,863,865 A * | 1/1999 | Lee et al. | 504/271 |
| 6,087,305 A * | 7/2000 | Kober et al. | 504/362 |
| 2005/0266999 A1* | 12/2005 | Frisch et al. | 504/365 |

FOREIGN PATENT DOCUMENTS

| | | |
|---|---|---|
| CH | 459 658 A | 7/1968 |
| DE | 29 24 403 | 12/1980 |
| EP | 0 048 436 A1 | 3/1982 |
| EP | 0 130 370 A1 | 1/1985 |
| EP | 0 297 305 A | 1/1989 |
| EP | 0 297 305 B1 | 12/1991 |
| EP | 0 499 798 A1 | 8/1992 |
| EP | 1 095 564 A | 5/2001 |
| GB | 1047601 | 11/1966 |
| WO | WO 96/22692 | 8/1996 |
| WO | WO 2004/021789 A | 3/2004 |
| ZA | 96/0502 | 10/1996 |

OTHER PUBLICATIONS

Aldrich-Markham, S., Nurse Crops for Erosion Control in Newly-Planted Grass Seed Fields, 2004, <http://cropandsoil.oregonstate.edu/seed-ext/Pub/2004/16.pdf>.*
Bennett, A., Effect of Preharvest Desiccants on Weed Seed Production and Viablility, Weed Technology, 200, vol. 14:530-538.*
Luo, Q., Stabilization of Alumina Slurry for Chemical-Mechanical Polishing of Copper, Langmuir, 1996, 12, p. 3563-3566.*
Bennett, A., Effect of Preharvest Desiccants on Weed Seed Production and Viability, Weed Technology, 2000, vol. 14:530-538.*
Database Chembs Online!; Database Accession No. 116:230204, XP002359292; Jun. 1992.

* cited by examiner

*Primary Examiner* — Rebecca Prouty
*Assistant Examiner* — Danielle Sullivan
(74) *Attorney, Agent, or Firm* — Frommer Lawrence & Haug LLP

(57) ABSTRACT

Liquid aqueous formulations of water-soluble active crop protectant ingredients which comprise
(a) one or more water-soluble active crop protectant ingredients (type (a) ingredients),
(b) one or more water-dispersed active crop protectant ingredients (type (b) ingredients),
(c) one or more surfactants from the class of the polyacrylic acid derivatives,
(d) one or more aluminum silicates as stabilizer(s),
(e) if desired, further anionic or nonionic, cationic and/or zwitterionic surfactants,
(f) if desired, other customary formulation assistants, and
(g) water
are suitable as stable coformulations for use in crop protection.

20 Claims, No Drawings

CONCENTRATED, WATER-BASED DISPERSIONS FOR CROP PROTECTION

The invention relates to the technical field of preparations (formulations) for active ingredients in the crop protection field (agrochemical active ingredients), particularly to concentrated aqueous formulations of two or more active crop protectant ingredients (coformulations), and especially to aqueous formulations of saltlike active crop protectant ingredients, such as glufosinate-ammonium, with largely water-insoluble active crop protectant ingredients.

Crop protectant compositions can be formulated in principle in many different ways, with the possibility of the characteristics of the active ingredients and the nature of the formulation giving rise to problems in terms of stability, efficacy, and applicability of the formulations. Moreover, certain formulations are more advantageous on economic and environmental grounds than others.

Water-based formulations generally have the advantage that they require a low fraction of organic solvents, or none at all. On the other hand, the distribution of the constituents in such formulations is often inadequate unless appropriate combinations of auxiliaries are used. The performance properties of such formulations frequently depend on a large number of variable parameters, making it impossible simply to select components of known systems and to combine them with the active ingredients intended for new formulation, if the resultant formulation is to be biologically active, stable on storage, and ideal from the applications standpoint.

Standard formulations, therefore, are rarely suitable for meeting particular requirements, and it is necessary to take the trouble, involving a great deal of experimental work, to develop an appropriate formula.

By aqueous concentrated formulations are meant here, primarily, those which have water as their carrier phase. This is not intended to rule out the possibility of the presence of organic solvents in dissolved or stably emulsified form. Organic solvents that are suitable in such a case are principally those which are fully miscible with water. The formulations preferably contain no water-immiscible organic solvents. The active ingredients can be in solution in the aqueous formulations or can be dispersed in the form of small particles, or partly in solution and partly dispersed. Examples of formulations comprising an active ingredient in dissolved form (glufosinate-ammonium) are known from EP-A-0048436. Examples of formulations comprising active ingredients (e.g., isoproturon) dispersed in water are described in DE-A-2924403. EP-A-0297305 discloses coformulations of an active substance present in dissolved form (e.g., glufosinate, glyphosate, paraquat, CMPP, 2,4-D, 2,4-DP, MCPA) and at least one active substance present in dispersed form (e.g., triazines such as simazine, atrazine, cyanazine, phenylureas such as isoproturon, chlortoluron, linuron, monolinuron, diuron, pyridines such as trichlopyr or fluroxypyr, hydroxybenzonitriles such as bromoxynil and ioxynil, diphenyl ethers such as oxyfluorfen or deltamethrin, carbendazim or endosulfan).

In addition to the van der Waals' forces, and electric, steric and entropy effects, shape factors play a large part in maintaining the physical stability of dispersed systems over a prolonged period of time. Good storage properties can also be achieved with corresponding suitable stabilizers, thickeners, thixotropic auxiliaries, etc.

The object which existed was to provide a concentrated, water-based coformulation suitable for the combination of one or more water-soluble active ingredients and one or more water-dispersed active ingredients.

The invention provides liquid aqueous crop protectant compositions which comprise (a) one or more water-soluble active crop protectant ingredients (type (a) active ingredients),
(b) one or more water-dispersed active crop protectant ingredients (type (b) active ingredients),
(c) one or more surfactants from the class of the polyacrylic acid derivatives,
(d) one or more aluminum silicates as stabilizer(s),
(e) if desired, further anionic or nonionic, cationic and/or zwitterionic surfactants,
(f) if desired, other customary formulation assistants, and
(g) water.

The present invention relates to a system in which one or more active ingredients are in solution in the carrier phase and one or more active ingredients are dispersed as fine solid particles in the carrier phase. The carrier phase itself is composed preferably of water, and then may also include the surfactants and/or viscosity modifiers and/or other formulation assistants such as frost protectants and/or defoamers and/or bactericides and/or other agents that stabilize the system.

Also known is a formulation in which, instead of finely dispersed particles, finely emulsified droplets with the relevant active ingredients in dissolved form are described (WO 96/22692). A disadvantage here is that no solvent-free formulation based only on water is obtained.

As their water-dissolved active ingredients (or else combinations thereof) it is possible for the aqueous formulations of the invention to comprise, for example, ingredients from the group of the water-soluble active crop protectant ingredients such as glufosinate, glyphosate, paraquat, diquat and the like such as MCPA, CMPP, ioxynil, bromoxynil, 2,4-D, TCA, 2,4-DP and, preferably, their salts.

Preference is given to formulations comprising type (a) ingredients from the group consisting of one or more compounds of the formula (1) or salts thereof, $$H_3C-\underset{\underset{OH}{|}}{\overset{\overset{O}{\|}}{P}}-CH_2-CH_2-\underset{\underset{NH_2}{|}}{CH}-\overset{\overset{O}{\|}}{C}-Z_1 \quad (1)$$

in which
$Z_1$ is a radical of the formula $-OM$, $-NHCH(CH_3)CONHCH(CH_3)CO_2M$ or $-NHCH(CH_3)CONHCH[CH_2CH(CH_3)_2]CO_2M$, where
$M = H$ or a salt-forming cation,
and/or one or more compounds of the formula (2) or salts thereof, $$R_2O-\underset{\underset{OR_3}{|}}{\overset{\overset{O}{\|}}{P}}-CH_2-NH-CH_2-Z_2 \quad (2)$$

in which
$Z_2$ is a radical of the formula CN or $CO_2R_1$, where $R_1 = Q$ or a salt-forming cation and
$Q = H$, alkyl, alkenyl, alkoxyalkyl or $C_6$-$C_{10}$ aryl which is unsubstituted or substituted and is preferably unsubstituted or substituted by one or more radicals from the group consisting of alkyl, alkoxy, halogen, $CF_3$, $NO_2$ and CN, and $R_2$ and $R_3$ each independently of one another are H, alkyl, $C_6$-$C_{10}$ aryl which is unsubstituted or substituted and is preferably unsubstituted or substituted by one or more radicals from the group consisting of alkyl, alkoxy, halogen, $CF_3$, $NO_2$ and CN, or are biphenylyl or a salt-forming cation.

Preferably, the carbon-containing radicals in connection with Q, $R_2$ or $R_3$, respectively, have up to 10 carbon atoms, particularly preferred up to 6 carbon atoms.

The compounds of the formula (1) contain an asymmetric carbon atom. The L enantiomer is regarded as the biologically active isomer. The formula (1) therefore embraces all stereoisomers and mixtures thereof, especially the racemate and the biologically active enantiomer in each case. Examples of active ingredients of the formula (1) are as follows:
glufosinate and its ammonium salt in racemic form, i.e., 2-amino-4-[hydroxy(methyl)phosphinoyl]butanoic acid and its ammonium salt,
the L enantiomer of glufosinate and its ammonium salt,
bilanafos/bialaphos, i.e., L-2-amino-4-[hydroxy(methyl)phosphinoyl]butanoyl-L-alaninyl-L-alanine and its sodium salt.

The racemate of glufosinate-ammonium is, on its own, customarily applied at rates of between 200 and 1000 g a.i./ha (i.e., grams of active ingredient per hectare). Glufosinate-ammonium at these rates is especially effective when it is taken up via green parts of the plant; see "The Pesticide Manual" 13th Edition, British Crop Protection Council 2003. Glufosinate-ammonium is used predominantly for controlling broadleaf and gramineous weeds in plantation crops and on uncultivated land and also, by means of special application techniques, for inter-row control in agricultural ground crops such as maize, cotton, etc. Its use is also of increasing importance in transgenic crops which are tolerant or resistant to the active ingredient.

The compounds of the formula (2) are N-(phosphonoalkyl) glycine compounds and hence are derivatives of the amino acid glycine. The herbicidal properties of N-(phosphonomethyl)glycine (glyphosate) are described for example in U.S. Pat. No. 3,799,758.

In crop protectant formulations, glyphosate is used generally in the form of the water-soluble salts, particular importance attaching, in connection with the present invention, to the isopropylammonium salt; see "The Pesticide Manual" 13th Edition, British Crop Protection Council 2003.

The fraction of the active ingredients (a) may be varied widely and is generally in the range from 1% to 60%, preferably from 5% to 55% and more preferably from 8% to 35% by weight of active ingredient (a), based on the weight of the formulation.

Suitable type (b) active ingredients, present as finely ground particles in the dispersed phase, include, for example, the following:
herbicides from the group of the diphenyl ethers, carbamates, thiocarbamates, triphenyltin and tributyltin compounds, haloacetanilides, phenoxyphenoxy-alkanecarboxylic acid derivatives and heteroaryloxyphenoxyalkanecarboxylic acid derivatives, such as quinolyloxy-, quinoxalyloxy-, pyridyloxy-, benzoxalyloxy- and benzothiazolyloxyphenoxyalkanecarboxylic esters.
Correspondingly insoluble active ingredients as well, from classes which normally include active ingredients of different solubilities, are suitable, examples being active substances from the group of the cyclohexanedione derivatives, imidazolinones, pyrimidyloxypyridinecarboxylic acid derivatives, pyrimidyloxybenzoic acid derivatives, sulfonylureas, triazolopyrimidinesulfonamide derivatives and S-(N-aryl-N-alkylcarbamoylmethyl)dithiophosphoric esters, examples being active ingredients such as oxyfluorfen, lactofen, bifenox, fluoroglycofen, acifluorfen, fomesafen, diclofop-methyl, fenoxaprop-ethyl or fenoxaprop-P-ethyl.

The stated common names for the active ingredients, such as glufosinate, glyphosate, oxyfluorfen, MCPA, 2,4-D and so on, are common knowledge; see, for example, "The Pesticide Manual" 13th Edition, British Crop Protection Council 2003; they also embrace the known derivatives such as salts, esters and amides, and particularly the commercially customary forms.

In accordance with the herbicides stated it is also possible for suitable active ingredients to be those from the group of the safeners, plant growth regulators, insecticides and fungicides as component (b) and/or, in the event of good water-solubility as components (a).

The type of active ingredients (a) and (b) used determine the type of pests which can be controlled by application of the crop protection compositions or agrochemical formulations. In case of herbicides the pests are undesired plants.

The fraction of the active ingredients (b) in the formulation is generally in the range from 0.5% to 30%, preferably from 1% to 20% and in particular from 1% to 15% by weight of active ingredient, based on the weight of the formulation.

The weight ratio of dissolved active ingredients (a) to dispersed active ingredient(s) (b) in the formulation depends advantageously on the efficacy of the individual active ingredients and on their physical characteristics and amounts for example to 15:1 to 1:12, preferably 10:1 to 1:4.

In accordance with the invention the formulation is stabilized by a combination of components (c) and (d). Only after a multiplicity of experiments was it found, surprisingly, that aqueous coformulations with the stated, physically very different active ingredients (a) and (b), particularly if the stated active ingredients (a) are in solution as salts and the formulations additionally have a high fraction of wetting agent, can be stabilized very effectively by a combination of a surfactant from the class of the polyacrylic acid derivatives (component (c)) and a stabilizer from the group of the aluminum silicates (component (d)).

Suitable components (c) include polyacrylic acid derivatives such as, for example
®Sokalan CP10 (the sodium salt of a modified polyacrylic acid; BASF)
polyacrylates from the series ®Sokalan CP 13 S, PA 15, PA 20, PA 20 S, PA 25, PA 30, PA 40, PA 50, PA 70 PN, 80 S (BASF);
polyacrylate copolymers such as those from the ®Carbopol series (Noveon Inc., formerly B.F. Goodrich Co.);
ammonium and sodium polyacrylates from the ®Degapas series (Degussa);
Dispersant HB (sodium polyacrylate, Rhodia), and
®Permulsin (Na polyacrylate, Polygon Chemie).

The stabilizer from the group of the aluminum silicates (component (d)) is preferably a mineral fiber, such as a fiber-like magnesium and aluminum silicate attapulgite, preferably ®Clarsol ATC (from CECA, Düsseldorf, Germany). Also suitable are ®Bentone EW (from Rheox) or Attapulgit Select 615® (from Oil Dry), which likewise comprise attapulgite as their base material.

The polyacrylic acid derivative (c) is present in the formulation generally in the range from 0.05% to 15%, preferably at 0.1% to 10% and in particular at 0.4% to 5% by weight. The aluminum silicate (d) is generally present in the formulation in the range from 0.05% to 15%, preferably from 0.1% to 8% and in particular from 0.3% to 5% by weight.

The weight ratio of surfactant to aluminum silicate amounts preferably to 15:1 to 1:20, in particular 10:1 to 1:14.

The formulations of the invention comprise as component (e), if desired, anionic, cationic or zwitterionic and/or nonionic surface-active compounds (surfactants) which are able to contribute to improved stability, improved plant availability or improved activity of the formulated crop protectants.

Examples of anionic surfactants are as follows (where EO=ethylene oxide units, PO=propylene oxide units, and BO=butylene oxide units):

e1-1) anionic derivatives of fatty alcohols having 10-24 carbon atoms with 0-60 EO and/or 0-20 PO and/or 0-15 BO in any order, in the form of ether carboxylates, sulfonates, sulfates and phosphates and their inorganic (e.g., alkali metal and alkaline earth metal) and organic salts (based, for example, on amines or alkanolamines), such as Genapol® LRO, Sandopan® grades, Hostaphat®/Hordaphos® grades from Clariant;

e1-2) anionic derivatives of copolymers composed of EO, PO and/or BO units with a molecular weight of 400 to $10^8$, in the form of ether carboxylates, sulfonates, sulfates and phosphates and their inorganic (e.g., alkali metal and alkaline earth metal) and organic salts (based, for example, on amines or alkanolamines);

e1-3) anionic derivatives of alkylene oxide adducts of $C_1$-$C_9$ alcohols, in the form of ether carboxylates, sulfonates, sulfates and phosphates and their inorganic (e.g., alkali metal and alkaline earth metal) and organic salts (based, for example, on amines or alkanolamines);

e1-4) anionic derivatives of fatty acid alkoxylates, in the form of ether carboxylates, sulfonates, sulfates and phosphates and their inorganic (e.g., alkali metal and alkaline earth metal) and organic salts (based, for example, on amines or alkanolamines).

Preferred anionic surfactants here are alkyl polyglycol ether sulfates, especially fatty alcohol diethylene glycol ether sulfate (e.g., Genapol LRO®, Clariant), or alkyl polyglycol ether carboxylates (e.g., 2-(isotridecyloxypolyethyleneoxy)ethyl carboxymethyl ether, Marlowet 4538®, Hüls).

Examples of cationic or zwitterionic surfactants are as follows (where EO=ethylene oxide units, PO=propylene oxide units and BO=butylene oxide units):

e2-1) alkylene oxide adducts of fatty amines, quaternary ammonium compounds having 8 to 22 carbon atoms ($C_8$-$C_{22}$) such as, for example, the Genamin® C, L, O, and T grades from Clariant;

e2-2) surface-active zwitterionic compounds such as taurides, betaines and sulfobetaines in the form of Tegotain® grades from Goldschmidt, Hostapon®T and Arkopon®T grades from Clariant.

Examples of nonionic surfactants are:

e3-1) fatty alcohols having 10-24 carbon atoms with 0-60 EO and/or 0-20 PO and/or 0-15 BO in any order. Examples of compounds of this kind are Genapol® C, L, O, T, UD, UDD, and X grades from Clariant, Plurafac® (and Lutensol® A, AT, ON and TO grades from BASF, Marlipal®24 and O13 grades from Condea, Dehypon® grades from Henkel, Ethylan® grades from Akzo-Nobel such as Ethylan CD 120;

e3-2) fatty acid alkoxylates and triglyceride alkoxylates such as the Serdox® NOG grades from Condea or the Emulsogen® grades from Clariant;

e3-3) fatty acid amide alkoxylates such as the Comperlan® grades from Henkel or the Amam® grades from Rhodia;

e3-4) alkylene oxide adducts of alkynediols such as the Surfynol® grades from Air Products; sugar derivatives such as amino and amido sugars from Clariant;

e3-5) glucitols from Clariant;

e3-6) silicone- and/or silane-based surface-active compounds such as the Tegopren® grades from Goldschmidt and the SE® grades from Wacker, and also the Bevaloid®, Rhodorsil® and Silcolapse® grades from Rhodia (Dow Corning, Reliance, GE, Bayer), e3-7) surface-active sulfonamides, e.g., from Bayer;

e3-8) surface-active polyacrylic and polymethacrylic derivatives such as the Sokalan® grades from BASF;

e3-9) surface-active polyamides such as modified gelatins or derivatized polyaspartic acid from Bayer, and derivatives thereof, e3-10) polyvinyl surfactant compounds such as modified PVP such as the Luviskol® grades from BASF and the Agrimer® grades from ISP or the derivatized polyvinyl acetates such as the Mowilith® grades from Clariant or the polyvinyl butyrates, such as the Lutonal® grades from BASF, the Vinnapas® and the Pioloform® grades from Wacker, or modified polyvinyl alcohols such as the Mowiol® grades from Clariant, e3-11) surface-active polymers based on maleic anhydride and/or reaction products of maleic anhydride, and also maleic anhydride copolymers and/or reaction products of maleic anhydride copolymers, such as the Agrimer® VEMA grades from ISP, e3-12) surface-active derivatives of montan waxes, polyethylene waxes, and polypropylene waxes, such as the Hoechst® waxes or the Licowet® grades from Clariant, e3-13) sorbitan esters in the form of the Span® or Tween® grades from Uniqema, e3-14) surface-active cellulose derivatives, algin derivatives, pectin derivatives and guar derivatives such as the Tylose® grades from Clariant, the Manutex® grades from Kelco and guar derivatives from Cesalpine, e3-15) polyol-based alkylene oxide adducts such as Polyglykol® grades from Clariant;

e3-16) surface-active polyglycerides and their derivatives from Clariant, e3-17) alkylpolysaccharides and mixtures thereof such as those, for example, from the ®Atplus series (Uniqema) with or without addition of inorganic salts such as ammonium sulfate, e3-18) alkylpolyglycosides in the form of the APG® grades from Henkel, an example being ®Plantaren APG 225 (fatty alcohol $C_8$-$C_{10}$ glucoside), e3-19) cyclodextrin esters or cyclodextrin ethers from Wacker, and e3-20) alkylpolyglycoside/alkylpolysaccharide mixtures based on $C_8$-$C_{10}$ fatty alcohol such as ®Glucopon 225 DK and ®Glucopon 215 CSUP (Cognis).

As component (f), the formulations of the invention comprise customary formulation assistants, examples being inert materials, such as stickers, wetters, dispersants, emulsifiers, penetrants, preservatives, and frost protectants, fillers, carriers and colorants, evaporation inhibitors and pH modifiers (buffers, acids, and bases) or viscosity modifiers (e.g., thickeners) or defoamers. The addition of inorganic salts may be of advantage particularly in combination with certain surfactants.

Suitable formulation assistants also include organic solvents, especially water-miscible organic solvents, examples being aliphatic alcohols, such as lower alkanols, for example, such as methanol and ethanol or polyhydric alcohols such as ethylene glycol and glycerol, polar ethers such as alkylene glycol monoalkyl and dialkyl ethers, such as propylene glycol monomethyl ether, propylene glycol monoethyl ether, ethylene glycol monomethyl ether or monoethyl ether, diglyme and tetraglyme;

amides such as dimethylformamide (DMF), dimethylacetamide, dimethylcaprylamide, dimethylcapramide (®Hallcomide) and N-alkylpyrrolidones;

ketones such as acetone;

nitriles such as acetonitrile, and sulfoxides and sulfones such as dimethyl sulfoxide (DMSO) and sulfolane.

Preference is given here to largely water-miscible organic solvents such as, for example, N-methylpyrrolidone (NMP), dimethylformamide (DMF), dimethylacetamide (DMA) or Dowanol® PM (propylene glycol monomethyl ether).

The organic solvents ought only to be used in amounts such that the aqueous phase is stable, preferably in the form of a thermodynamically stable aqueous solution.

Customary formulation assistants (f) are, for example, the stated inert materials, frost protectants, evaporation inhibitors, preservatives, colorants, etc.; preferred formulation assistants (f) are frost protectants and evaporation inhibitors such as glycerol or ethylene glycol, in an amount from 2% to 10% by weight, for example, and preservatives, e.g., Mergal K9N® (Riedel) or Cobate C®, defoamers.

In the case of the aqueous formulations it is often advantageous to add defoamers. Suitable defoamers include all customary defoamers, preferably silicone-based defoamers, such as silicone oils, for example.

Preferred defoamers are those from the group of the linear polydimethylsiloxanes having an average dynamic viscosity, measured at 25° C., in the range from 1000 to 8000 mPas (mPas=millipascal second), preferably 1200 to 6000 mPas, and containing silica. Silica embraces forms/modifications such as polysilicic acids, meta-silicic acid, ortho-silicic acid, silica gel, silicic acid gels, kieselguhr, precipitated $SiO_2$, etc. Defoamers from the group of the linear polydimethylsiloxanes contain as their chemical backbone a compound of the formula HO—[Si(CH$_3$)$_2$—O—]$_n$—H, in which the end groups are modified, by etherification for example, or in general are attached to the groups —Si(CH$_3$)$_3$.

The amount of silica can be modified within a wide range and is generally in the range from 0.1 to 10 percent, preferably 0.2 to 5 percent, in particular 0.2% to 2% by weight of silica, based on the weight of polydimethylsiloxane.

Examples of defoamers of this kind are ®Rhodorsil Antifoam 416 (Rhodia) and ®Rhodorsil Antifoam 481 (Rhodia).

®Rhodorsil Antifoam 416 is a medium-viscosity silicone oil having a dynamic viscosity at 25° C. of about 1500 mPas and containing surfactant and silica. The surfactant content lowers the density as compared with the unadditized silicone oil, the density being about 0.995 g/cm$^3$.

®Rhodorsil Antifoam 481 is a medium-viscosity silicone oil having a dynamic viscosity at 25° C. of about 4500 mPas and containing silica. The density is about 1.045 g/cm$^3$. Further defoamers from the group of the silicones are Rhodorsil 1824, Antimussol 4459-2 (Clariant), Defoamer V 4459 (Clariant), and SE Visk and AS EM SE 39 (Wacker). The silicone oils can also be used as emulsions.

The assistants needed to prepare the formulations indicated above, such as surfactants in particular, are known in principle and are described for example in McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte", Wiss. Verlagsgesellschaft, Stuttgart 1976; Winnacker-Küchler, "Chemische Technologie", Volume 7, C. Hanser-Verlag, Munich, 4th Edition 1986, and references cited in each of these.

By means of the mixtures of components it is accordingly possible to prepare preferably aqueous formulations of water-soluble (saltlike) active crop protectant ingredients, such as glufosinate-ammonium, which comprise (a) 1% to 60%, preferably 5% to 55% and in particular 8% to 55% by weight of water-soluble active crop protectant ingredients (type (a) ingredients), (b) 0.5% to 30%, preferably 1% to 20% and in particular 1% to 15% by weight of water-insoluble active crop protectant ingredients (type (b) ingredients), (c) 0.05% to 15%, preferably 0.1% to 10% and in particular 0.4% to 5% by weight of surfactants from the class of the polyacrylic acid derivatives, (d) 0.05% to 15%, preferably 0.1% to 8% and in particular 0.3% to 5% by weight of aluminum silicates as stabilizer(s), (e) 0 to 80%, preferably 0 to 70% and in particular 0 to 60% by weight of nonionic, anionic, cationic and/or zwitterionic surfactants, (f) 0 to 30%, preferably 0 to 20% and preferably 0 to 15% by weight of customary formulation assistants, and (g) 0.1% to 90%, preferably 5% to 70%, and preferably 10% to 50% by weight of water.

The formulations of the invention are prepared by conventional methods, by mixing and homogenizing water, active ingredient (a) in solid or already dissolved form, all assistants, and active ingredient (b) for ultimate dispersion, with stirring where appropriate, in a tank, for example, and comminuting the homogenized mixture to the requisite particle size by appropriate means, such as via colloid mills and/or ball mills, for example.

The formulations of the invention are distinguished by good storage properties and good flow behavior. A further advantage is the complete absence or low level of organic solvents. The coformulations, moreover, exhibit a high bioavailability and hence activity of the combined active crop protectant ingredients.

Consequently the formulations of the invention are especially suitable for use in crop protection: for example, where active herbicidal ingredients are included, for controlling unwanted plant growth both on uncultivated land and in tolerant crops.

Tables 1 and 2 below list examples of formulations of the invention. The formulations are stable on storage at 50° C. for more than 3 months, this stability including, in particular, stability of flow behavior.

TABLE 1

Formulations (inventive)

|  | 1 [1] | 2 | 3 | 4 | 5 | 6 | 7 | 8 | 9 |
|---|---|---|---|---|---|---|---|---|---|
| Glufosinate-ammonium (a.i.) | 21.74 | 21.55 | 21.55 | 21.55 | 21.55 | 21.55 | 21.55 | 21.55 | 21.55 |
| Oxyfluorfen (a.i.) | 4.51 | 4.47 | 4.38 | 4.47 | 4.38 | 4.56 | 4.43 | 4.38 | 4.43 |
| Genapol LRO paste | 35.00 | 30.00 | 30.00 | 30.00 | 30.00 | 30.00 | 30.00 | 30.00 | 30.00 |
| Sokalan CP 10 | 1.00 | 1.50 | 1.00 | 2.00 | 1.00 | 1.00 | 1.00 | 1.00 | 1.00 |
| Clarsol ATC | 2.50 | 3.00 | 3.00 | 3.00 | 3.00 | 3.00 | 3.00 | 3.00 | 3.00 |
| Propylene glycol | 10.00 | 10.00 | 10.00 | 10.00 | 10.00 | 10.00 | 10.00 | 6.00 | 5.00 |
| Rhodorsil 416 | 1.50 | 1.50 | 1.50 | 1.50 |  |  |  | 1.50 | 1.50 |
| Rhodorsil 481 [3] |  |  |  |  | 1.50 | 1.00 | 0.75 |  |  |
| Water (ad 100%) | ad 100 | ad 100 | ad 100 | ad 100 | ad 100 | ad 100 | ad 100 | ad 100 | ad 100 |

Key: See after Table 2

TABLE 2

Formulations (inventive)

|  | 10 [1] | 11 | 12 | 13 | 14 | 15 | 16 |
|---|---|---|---|---|---|---|---|
| Glufosinate-ammonium (a.i.) | 21.55 | 17.24 | 15.68 | 14.37 | 10.78 | 21.55 | 10.78 |
| Oxyfluorfen (a.i.) | 4.36 | 3.25 | 3.20 | 2.93 | 2.43 | 4.31 | 2.15 |
| Genapol LRO paste | 30.00 | 24.00 | 21.82 | 20.00 | 15.00 | 30.00 | 15.00 |
| Sokalan CP 10 | 1.00 | 0.80 | 0.73 | 0.67 | 0.50 | 1.00 | 0.50 |
| Clarsol ATC | 3.00 | 2.40 | 2.18 | 3.00 | 1.00 | 3.00 | 1.50 |
| Propylene glycol | 10.00 | 8.00 | 7.27 | 10.00 | 6.67 | 10.00 | 5.00 |
| Rhodorsil 416 |  | 1.20 | 1.09 | 1.00 | 0.75 |  |  |
| Rhodorsil 481 [3] | 0.60 |  |  |  |  | 1.50 | 0.75 |
| Water (ad 100%) | ad 100 | ad 100 | ad 100 | ad 100 | ad 100 | ad 100 | ad 100 |

(a.i.) Amount based on active ingredient
[1] The columns list the compositions of formulations 1 to 9 (in Table 1) and 10 to 16 (in Table 2), the respective line containing the amount of the component identified in the first column, in weight percent;
®Genapol LRO paste = $C_{12}/C_{14}$ fatty alcohol diethylene glycol ether sulfate, used as a 68% strength aqueous solution, Clariant)
®Sokalan CP10 = modified polyacrylic acid, sodium salt; BASF)
®Clarsol ATC = a fiberlike magnesium and aluminum silicate attapulgite
®Rhodorsil 481 (polydimethylsiloxane with silica gel, Rhodia)
®Rhodorsil 416 (polydimethylsiloxane with silica gel and surfactant, Rhodia)
The amount of water is stated as ad 100% and also includes small amounts of nonaqueous secondary constituents that may be present in certain components used; for example, colorants, preservatives, etc.

BIOLOGICAL EXAMPLES

The formulations according to Tables 1 and 2 were diluted with water and applied at a water application rate of 200 I/ha to uncultivated land which contained a spectrum of weed plants that had emerged under natural conditions. Evaluation after 4 weeks revealed that the green parts of the weed plants had died off and therefore that effective control of the weed plants had been achieved.

What is claimed is:

1. A liquid aqueous crop protectant composition which comprises as components (a) to (g):
   (a) 1% to 60% by weight of one or more water-soluble active ingredients selected from the group consisting of the salts of glufosinate, glyphosate, paraquat, diquat, MCPA, CMPP, ioxynil, bromoxynil, 2,4-D, TCA, 2,4 DP and salts thereof,
   (b) 0.5% to 30% by weight of water-insoluble active ingredient selected from the group consisting of oxyfluorfen, lactofen, bifenox, fluoroglycofen, fomesafen, diclofop-methyl, fenoxaprop-ethyl and fenoxaprop-P-ethyl,
   (c) 0.05% to 15% by weight of one or more surfactants from the class of the polyacrylic acid derivatives,
   (d) 0.05% to 15% by weight of one or more aluminum silicates as stabilizer(s),
   (e) 0 to 80% by weight of nonionic, anionic, cationic and/or zwitterionic surfactants,
   (f) 0 to 30% by weight of customary formulation assistants, and
   (g) 0.1% to 90% by weight of water.

2. The crop protectant composition as claimed in claim 1, comprising as a component (a) ingredient a salt of glufosinate.

3. The crop protectant composition as claimed in claim 2, comprising as a component (a) ingredient glufosinate-ammonium.

4. The crop protectant composition as claimed in claim 1, comprising as a component (b) ingredient an active ingredient selected from the group consisting of oxyfluorfen, lactofen, bifenox, fluoroglycofen, and fomesafen.

5. The crop protectant composition as claimed in claim 4, comprising as a component (b) ingredient oxyfluorfen.

6. The crop protectant composition as claimed in claim 1, wherein the weight ratio of component (a) to component (b) amounts to 15:1 to 1:12.

7. The crop protectant composition as claimed in claim 1, wherein the weight ratio of surfactant (c) to aluminum silicate (d) amounts to 15:1 to 1:20.

8. The crop protectant composition as claimed in claim 1, wherein component (a) is glufosinate ammonium and component (b) is oxyfluorfen.

9. The crop protectant composition as claimed in claim 1, comprising as a component (b) ingredient an active ingredient selected from the group consisting of diclofop-methyl, fenoxaprop-ethyl and fenoxaprop-P-ethyl.

10. The crop protectant composition as claimed in claim 1, wherein the composition is an aqueous suspension wherein any organic solvent present is miscible with water or no organic solvent is present.

11. The crop protectant composition as claimed in claim 10, which comprises
- (a) 5% to 55% by weight of water-soluble active ingredients of component (a),
- (b) 1% to 20% by weight of water-insoluble active ingredients of component (b),
- (c) 0.1% to 10% by weight of surfactants from the class of the polyacrylic acid derivatives,
- (d) 0.1% to 8% by weight of aluminum silicates as stabilizer(s),
- (e) 0 to 70% by weight of nonionic, anionic, cationic and/or zwitterionic surfactants,
- (f) 0 to 20% by weight of customary formulation assistants, and
- (g) 5% to 70% by weight of water.

12. The crop protectant composition as claimed in claim 11, wherein the weight ratio of component (a) to component (b) amounts to 15:1 to 1:12.

13. The crop protectant composition as claimed in claim 12, wherein the weight ratio of surfactant (c) to aluminum silicate (d) amounts to 15:1 to 1:20.

14. The crop protectant composition as claimed in claim 13, comprising as a component (a) ingredient a salt of glufosinate.

15. The crop protectant composition as claimed in claim 14, comprising as a component (a) ingredient glufosinate-ammonium.

16. The crop protectant composition as claimed in claim 15, comprising as a component (b) ingredient oxyfluorfen.

17. The crop protectant composition as claimed in claim 11, wherein component (a) is glufosinate ammonium and component (b) is oxyfluorfen.

18. A process for preparing a crop protectant composition as defined in claim 1, which comprises mixing components (a) to (f) and any further components present in the formulation with water (component (g)).

19. A method of controlling unwanted plant growth, which comprises applying an effective amount of a crop protectant composition as claimed in claim 1, comprising at least one active herbicidal ingredient, to the plants, parts of plants or the cultivation area.

20. A method of controlling a pest which comprises applying an effective amount of a crop protectant composition as claimed in claim 1 and comprising active ingredients effective against such pests, to the cultivation area or the non-crop area where the pest occurs.

\* \* \* \* \*